US010874509B2

(12) United States Patent
Braido et al.

(10) Patent No.: US 10,874,509 B2
(45) Date of Patent: Dec. 29, 2020

(54) COMMISSURE ATTACHMENT FEATURES FOR IMPROVED DELIVERY FLEXIBILITY AND TRACKING

(71) Applicant: St. Jude Medical, Cardiology Division, Inc., St. Paul, MN (US)

(72) Inventors: Peter N. Braido, Wyoming, MN (US); Mina S. Fahim, Shoreview, MN (US); Andrea L. McCarthy, Vadnais Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 133 days.

(21) Appl. No.: 15/892,749

(22) Filed: Feb. 9, 2018

(65) Prior Publication Data

US 2018/0161157 A1    Jun. 14, 2018

Related U.S. Application Data

(62) Division of application No. 14/475,874, filed on Sep. 3, 2014, now Pat. No. 9,968,448.

(60) Provisional application No. 61/873,418, filed on Sep. 4, 2013.

(51) Int. Cl.
*A61F 2/24* (2006.01)
*A61F 2/06* (2013.01)

(52) U.S. Cl.
CPC .... *A61F 2/2418* (2013.01); *A61F 2220/0075* (2013.01)

(58) Field of Classification Search
CPC .... A61F 2/2418; A61F 2/2412; A61F 2/2409; A61F 2/2445; A61F 2230/0069; A61F 2220/0075; A61F 2/246; A61F 2220/0025; A61F 2/24; A61F 2/07; A61F 2/2451; A61F 2/82

See application file for complete search history.

(56) References Cited

U.S. PATENT DOCUMENTS

| | | | |
|---|---|---|---|
| 4,349,102 A † | 9/1982 | Strongwater | |
| 6,244,444 B1 † | 6/2001 | Jacobus | |
| 8,092,523 B2 | 1/2012 | Li et al. | |
| 8,353,954 B2 | 1/2013 | Cai et al. | |
| 2004/0182801 A1 † | 9/2004 | Sedon | |
| 2009/0138079 A1 | 5/2009 | Tuval et al. | |
| 2010/0168839 A1 | 7/2010 | Braido et al. | |

(Continued)

FOREIGN PATENT DOCUMENTS

DE    29722970 U1 †  4/1998
FR     2793775 A1 † 11/2000

*Primary Examiner* — Ann Schillinger
(74) *Attorney, Agent, or Firm* — Lerner, David, Littenberg, Krumholz & Mentlik, LLP

(57) ABSTRACT

A prosthetic heart valve includes a collapsible and expandable stent having a proximal end and a distal end. A plurality of commissure attachment features ("CAFs") is disposed on the stent, with each CAF including a body and a plurality of eyelets. The eyelets may be arranged in a single column or in a plurality of rows and columns. The prosthetic heart valve also includes a collapsible and expandable valve assembly including a plurality of leaflets connected to the plurality of commissure attachment features. The bodies of the CAFs may include a number of other features including, for example, a slot extending between columns of eyelets.

12 Claims, 11 Drawing Sheets

(56) References Cited

U.S. PATENT DOCUMENTS

| | | | |
|---|---|---|---|
| 2010/0185277 A1* | 7/2010 | Braido | A61F 2/2412 |
| | | | 623/2.18 |
| 2010/0204781 A1* | 8/2010 | Alkhatib | A61F 2/2418 |
| | | | 623/1.26 |
| 2011/0208290 A1 | 8/2011 | Straubinger et al. | |
| 2012/0071969 A1 | 3/2012 | Li et al. | |
| 2012/0078347 A1 | 3/2012 | Braido et al. | |
| 2014/0005776 A1 | 1/2014 | Braido et al. | |

\* cited by examiner
† cited by third party

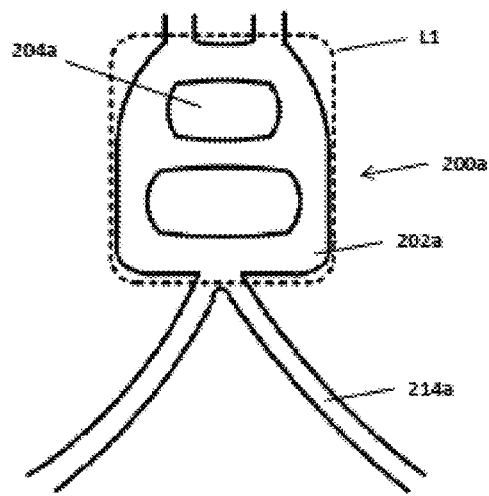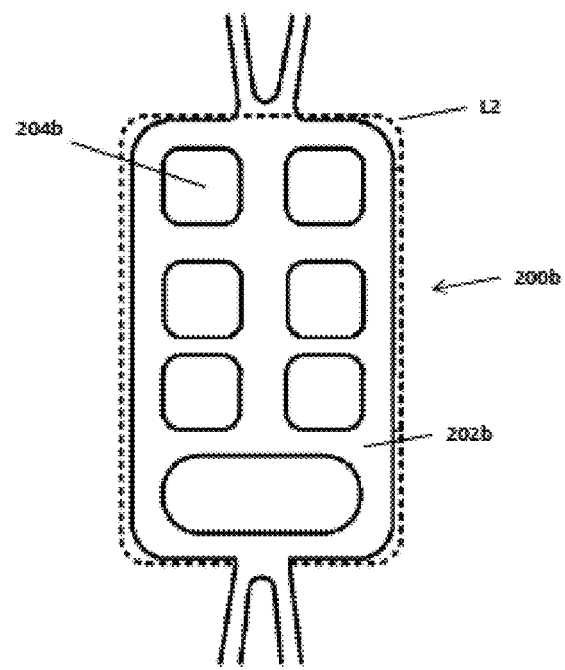
FIG. 2A
(PRIOR ART)
FIG. 2B
(PRIOR ART)

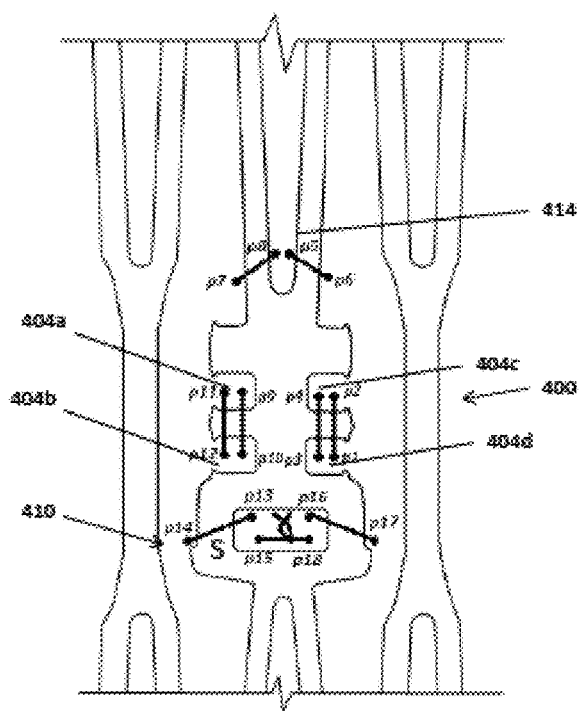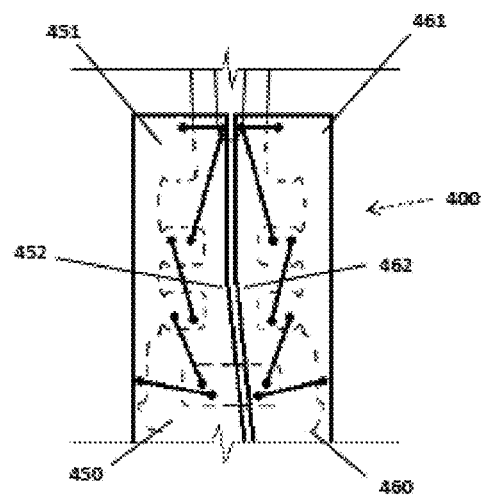
FIG. 4B                    FIG. 4C

COMMISSURE ATTACHMENT FEATURES FOR IMPROVED DELIVERY FLEXIBILITY AND TRACKING

CROSS-REFERENCE TO RELATED APPLICATIONS

The present application is a divisional of U.S. patent application Ser. No. 14/475,874, filed in Sep. 3, 2014, which claims the benefit of the filing date of U.S. Provisional Patent Application No. 61/873,418 filed Sep. 4, 2013, the disclosures of which are both hereby incorporated by reference herein.

BACKGROUND

The present disclosure relates to heart valve replacement and, in particular, to collapsible prosthetic heart valves. More particularly, the present disclosure relates to commissure attachment features used with collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

When using collapsible prosthetic heart valves, it may be desirable for the valve to be capable of collapsing (or crimping) to a small profile, such that, when collapsed, it may be contained within a relatively small delivery system. The ability of a collapsible prosthetic heart valve to collapse to a small profile may be at least partially dependent on the amount of material forming the stent supporting the valve. Similarly, the flexibility of the collapsible prosthetic heart valve may be dependent, at least in part, on the amount of material, as well as the geometry of material, in the stent supporting the valve. Increased flexibility may be desirable, for example, because increased flexibility of the collapsible valve may lead to increased flexibility in the delivery system. Increased flexibility in the delivery system may lead to reduced likelihood of vascular trauma or stroke as a result of delivery, and may facilitate the tracking of the aortic arch by the delivery system during delivery. Generally, tracking refers to the ability of the delivery system and/or collapsible prosthetic heart valve to bend or otherwise change shape with respect to the constraints of the anatomy through which they are moving. Preferably, design changes that reduce the profile of the collapsible valve and/or increase flexibility do not significantly negatively affect other characteristics of the valve, such as valve durability and hemodynamics.

BRIEF SUMMARY

In one embodiment, a prosthetic heart valve includes a collapsible and expandable stent having a proximal end and a distal end, the stent including a plurality of struts defining a plurality of open cells. The valve also includes a plurality of commissure attachment features disposed on the stent, each commissure attachment feature including a body and a plurality of eyelets arranged in at least two rows and at least two columns. The body may include a slot extending from a distal end of the body between two of the columns of eyelets toward a proximal end of the body, the slot dividing the body into a first portion and a second portion. The valve may further include a collapsible and expandable valve assembly including a plurality of leaflets connected to the plurality of commissure attachment features, In another embodiment, a prosthetic heart valve includes a collapsible and expandable stent having a proximal end and a distal end, the stent including a plurality of struts defining a plurality of open cells. The valve also includes a plurality of commissure attachment features disposed on the stent, each commissure attachment feature including a body having a longitudinal axis and a plurality of eyelets arranged in one column, the plurality of eyelets including a generally rectangular proximalmost eyelet and at least two generally rectangular eyelets positioned distal to the proximalmost eyelet. The at least two distal eyelets may each be wider than the proximalmost eyelet. The valve may further include a collapsible and expandable valve assembly including a plurality of leaflets connected to the plurality of commissure attachment features.

In still a further embodiment, a prosthetic heart valve includes a collapsible and expandable stent having a proximal end and a distal end, the stent including a plurality of struts defining a plurality of open cells. The valve may further include a plurality of commissure attachment features disposed on the stent, each commissure attachment feature including a body having a longitudinal axis and a plurality of eyelets arranged in at least two rows and at least two columns, at least one of the eyelets having an open side. The valve may further include a collapsible and expandable valve assembly including a plurality of leaflets connected to the plurality of commissure attachment features.

BRIEF DESCRIPTION OF THE DRAWINGS

FIG. 2A is a front view of a commissure attachment feature according to the prior art.

FIG. 2B is a front view of another commissure attachment feature according to the prior art.

FIG. 4B is a front view of suture attachments on the commissure attachment feature of FIG. 4A.

FIG. 4C is a rear view of the suture attachments in FIG. 4B.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient.

Figure 1A:
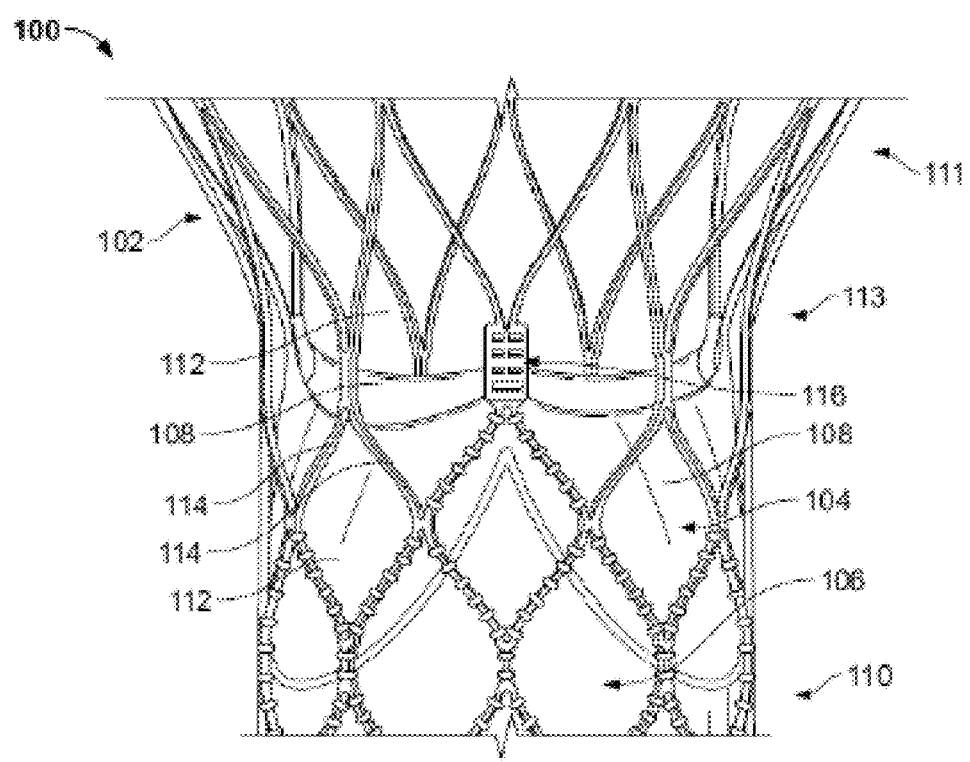
FIG. 1A is an enlarged partial side view of a collapsible prosthetic heart valve according to the prior art.

FIG. 1 shows a portion of a collapsible prosthetic heart valve 100 according to the prior art. Prosthetic heart valve 100 is designed to replace the function of a native aortic valve of a patient. Examples of collapsible prosthetic heart valves are described in U.S. Patent Publication No. 2012/0071969 and U.S. patent application Ser. No. 13/781,201, the entire disclosures of both of which are hereby incorporated by reference herein. The prosthetic heart valve has an expanded condition and a collapsed condition. Although the disclosure provided herein is applied to a prosthetic heart valve for replacing a native aortic valve, it is not so limited, and may be applied to prosthetic valves for replacing other types of cardiac valves.

Prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. Stent 102 may have an annulus section 110, an aortic section 111 and a transition section 113 disposed between the annulus section and the aortic section. Each of the annulus section 110, the transition section 113 and the aortic section 111 of stent 102 includes a plurality of cells 112 connected to one another around the stent. The annulus section 110 and the aortic section 111 of stent 102 may include one or more annular rows of cells 112 connected to one another. For instance, annulus section 110 may have two annular rows of cells 112. When prosthetic heart valve 100 is in the expanded condition, each cell 112 may be substantially diamond shaped. Regardless of its shape, each cell 112 is formed by a plurality of struts 114. For example, a cell 112 may be formed by four struts 114.

Stent 102 may include commissure attachment features ("CAF") 116. CAFs 116 may include eyelets for facilitating the suturing of a valve assembly 104, described below, to the stent 102.

Valve assemblies, such as valve assembly 104, are described in U.S. Pat. Nos. 8,092,523 and 8,353,954, the entire disclosures of both of which are hereby incorporated herein by reference. Valve assembly 104 may be attached in the annulus section 110 of stent 102, and may be wholly or partly formed of any suitable biological material or polymer. Examples of biological materials suitable for valve assembly 104 include, but are not limited to, porcine or bovine pericardial tissue. Examples of polymers suitable for valve assembly 104 include, but are not limited to, polyurethane and polyester.

Valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. Cuff 106 and/or the sutures used to attach valve assembly 104 to stent 102 may be formed from or include ultra-high-molecular-weight polyethylene, such as Force Fiber®, available from Teleflex Incorporated of Limerick, Pa. FIG. 1 shows cuff 106 disposed on the lumenal surface of annulus section 110 so as to cover part of the annulus section while leaving another part thereof uncovered. Cuff 106 may be attached to stent 102 by one or more strings or sutures passing through the cuff and around selected struts 114 of the stent. Valve assembly 104 may further include a plurality of leaflets 108 which collectively function as a one-way valve. A first edge of each leaflet 108 may be attached to stent 102 between two adjacent CAFs 116 by any suitable attachment means, such as by sutures, staples, adhesives, laser, heat or ultrasonic bonding or the like. For example, the first edge of each leaflet 108 may be sutured to stent 102 by passing strings or sutures through the cuff 106 of valve assembly 104. Leaflets 108 may be attached to stent 102 along at least some struts 114 of the stent and through the eyelets in CAFs 116 to enhance the structural integrity of valve assembly 104. A second or free edge of each leaflet 108 may coapt with the corresponding free edges of the other leaflets, thereby enabling the leaflets to function collectively as a one-way valve.

In operation, the embodiments of prosthetic heart valve 100 described above may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device. During delivery, the prosthetic heart valve is disposed inside the delivery device in the collapsed condition. The delivery device may be introduced into a patient using a transfemoral, transapical, transseptal, tranxaxillary or other approach. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

Figure 1B:
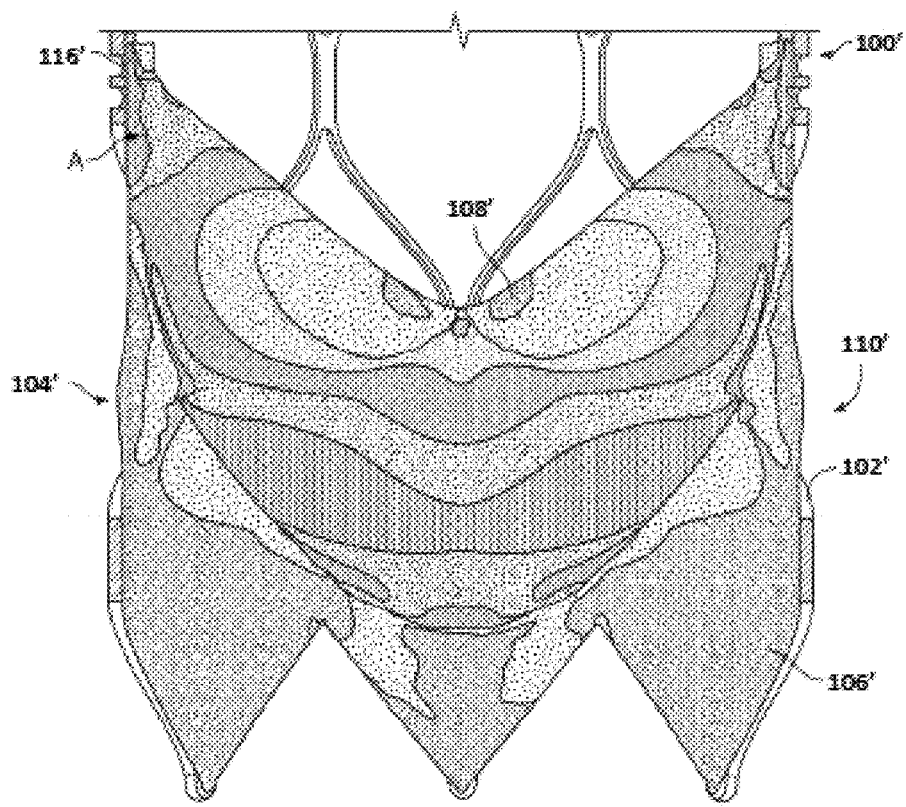
FIG. 1B is an enlarged, schematic side view of a portion of a prosthetic heart valve showing the distribution of load in the valve assembly.

As described above, prosthetic valve 100, and particularly stent 102, is preferably both flexible and capable of being collapsed to a small profile. One way to decrease the profile of valve 100 in the collapsed configuration and to increase the flexibility of the valve is by modifying CAFs 116. However, CAFs 116 may also need to be configured to robustly hold leaflets 108 attached thereto, for example, because the point of attachment between the leaflets and a CAF may be a point of high stress during normal valve operation. FIG. 1B is a partial side view of a prosthetic heart valve 100' having a stent 102' and a valve assembly 104' disposed in the annulus section 110' of the stent. Within heart valve 100', leaflets 108' are attached to cuff 106' via sutures. Specifically, FIG. 1B shows the load distribution in the valve assembly. When leaflets 108' coapt to form a closed configuration, load is transferred from the leaflet structure to the leaflet-commissure feature junction, as indicated by "A".

Generally, darker shading represents higher loads, although, most noteworthy, the load distribution diagram shows that high point loads are generated at regions "A" where the leaflets are joined to commissure features 116'. If the point loads at regions "A" are sufficiently high, the leaflets may tear from the commissure feature. Thus, regions A may be prone to failure. Thus, it would be preferable to have a CAF that is flexible and that facilitates crimping or collapsing of the valve to a small profile while still effectively distributing loads.

FIG. 2A illustrates a previous version of a CAF 200a coupled to struts 214a for attaching a valve assembly to the stent. Commissure feature 200a is formed of a body 202a having a pair of eyelets 204a. Leaflets (not shown) may be attached via sutures to CAF 200a through eyelets 204a and struts 214. Load is distributed across the area of CAF 200a as shown by dashed lines in FIG. 2A. Specifically, stress from the leaflets is distributed across area L1 of CAF 200a. FIG. 2B illustrates an alternate CAF 200b coupled to struts 214b according to the prior art. CAF 200b is formed of a body 202b having a plurality of eyelets 204b arranged in rows and/or columns. Leaflets (not shown) may be attached via sutures, glue, staples or any suitable means to CAF 200b through eyelets 204b and struts 214b. Stress from the leaflets is distributed across area L2 of CAF 200b, as shown by dashed lines in FIG. 2B. CAF 200b provides a larger area L2 across which the stress from the leaflets is distributed when compared to area L1 of CAF 200a. A larger area for distributing loads may decrease the chance of failure at the CAF-leaflet attachment.

FIGS. 3A-K and FIG. 4A illustrate several embodiments of CAFs according to aspects of the present disclosure. It will be appreciated that the commissure features described in these figures are exemplary and should not be considered limiting. Moreover, the described features in the following embodiments may be combined or modified in any desirable manner.

Figure 3A:
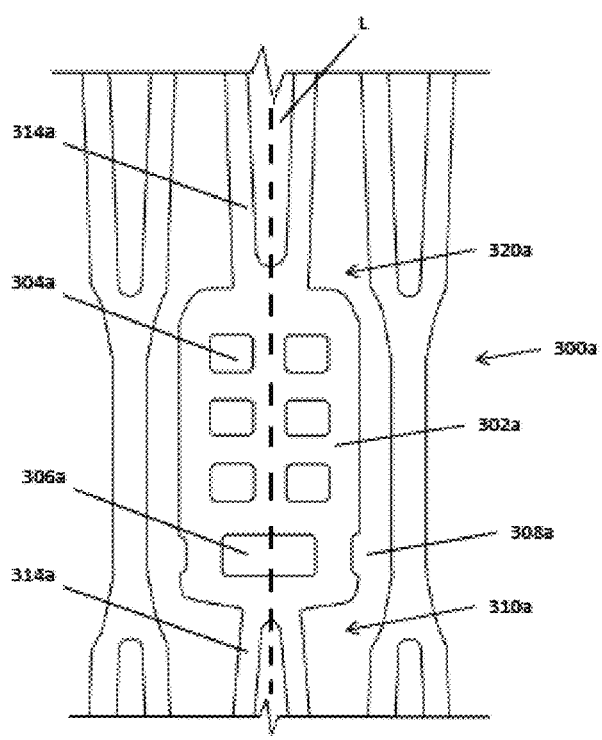
FIGS. 3A-3J are front views of different commissure attachment features according to different aspects of the disclosure.

FIG. 3A illustrates a CAF 300a according to one embodiment of the present disclosure. CAF 300a includes a body 302a having a proximal end 310a, a distal end 320a, and a plurality of eyelets 304a disposed therein. Body 302a is coupled to struts 314a at its proximal end 310a and distal end 320a. Specifically, the CAF 300a of FIG. 3A includes three rows of eyelets 304a along the length of body 302, each row including two eyelets so as to form two columns of eyelets. An elongated eyelet 306a is positioned proximal to the three rows of eyelets 304a. However, elongated eyelet 306a may be positioned above or in between other rows of eyelets 304a, depending, for example, on the particular suture pattern desired. The rows of eyelets 304a may be evenly spaced and of the same shape and size, as illustrated in FIG. 3A, so as to be symmetrical with respect to a longitudinal axis L of body 302a. As depicted, eyelets 304a, not including elongated eyelet 306a, are all in the shape of similarly sized squares. Leaflets (not shown) may be attached via sutures to CAF 300a through eyelets 304a and 306a. When placing a suture through the various eyelets 304a and 306a, the suture may be tied off in a knot to secure the suture. The knot may be positioned within the boundaries of elongated eyelet 306a, which may, for example, help protect the knot from being damaged by nearby structures. CAF 300a also includes recesses 308a disposed near the proximal end 310a of body 302a (adjacent the ends of elongated eyelet 306a). Recesses 308a may be formed as indentations or depressions in body 302a, and sutures may be wrapped around or disposed within the recesses. Such recesses may be useful in not only securing and guiding a suture, but also in protecting the suture from adjacent cells, a delivery system, or other anatomical bodies that may damage it.

Figure 3B:
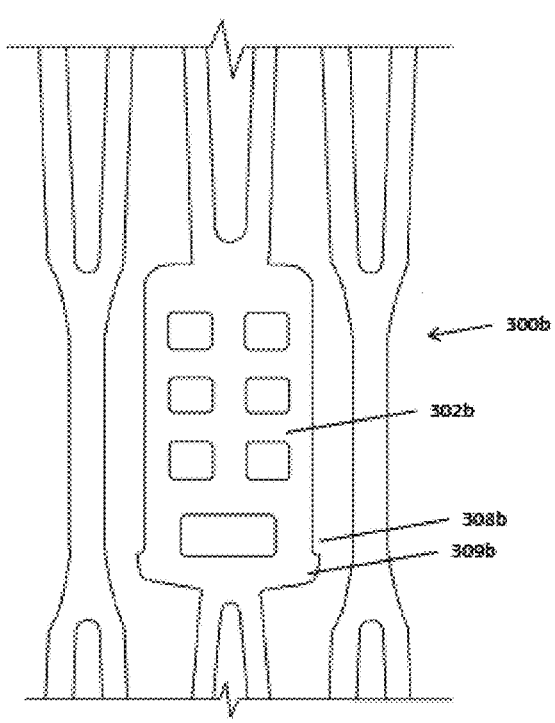

FIG. 3B illustrates a CAF 300b according to another embodiment of the disclosure. CAF 300b is similar to CAF 300a of FIG. 3A, with at least one exception. The body 302b of CAF 300b is narrower than the body 302a of FIG. 3A distal to the recess 308a. More particularly, to create body 302b of CAF 300b, the recess 308a of body 302a of CAF 300a is extended along the entire length of the body in the distal direction. Material proximal to recess 308b may be unmodified, leaving a recess that is bounded by material only on the proximal side. In other words, body 302b includes a pair of projections or ears 309b. The projections 309b may be positioned on each side of body 302b near a proximal portion thereof, with the projections extending circumferentially away from the longitudinal axis of the body farther than any other portion of the body distal to the projection. Projections 309b may function similarly to recesses 308a in that each projection may tend to keep a suture from sliding proximally along body 302b. In addition to preventing suture slippage, projections 309b may act as a stopper, such that when the stent is crimped or collapsed, adjacent struts that move closer to body 302b contact the projections, rather than contacting and possibly damaging the suture. In practice, the sutures may tend to migrate proximally, rather than distally, along body 302b, such that the lack of material distal to recess 308b does not make it significantly more likely that a suture will slip distally along body 302b. As described above, the removal of material from the body 302b of CAF 300b may result in the stent being able to collapse to a smaller profile, having better tracking capabilities, and being more flexible.

Figure 3C:
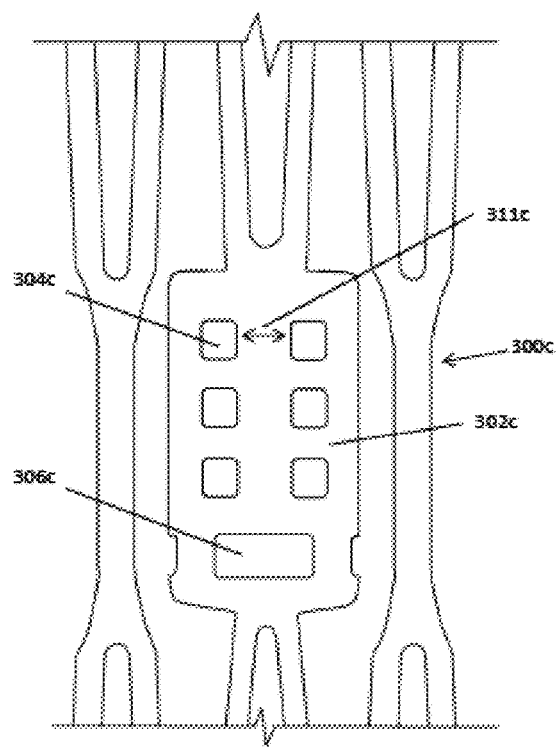

FIG. 3C illustrates a CAF 300c according to a further embodiment of the disclosure, which is similar to CAF 300a of FIG. 3A with at least one exception. Again, CAF 300c includes generally square or rectangular eyelets 304c, along with an elongated eyelet 306c. However, the eyelets 304c are smaller in size than eyelets 304a of CAF 300a. In particular, the width of eyelets 304c may be decreased such that the backbone 311c of body 302c of CAF 300c is wider. Backbone 311c may be at least partially defined by a portion of body 302c that exists between pairs of eyelets 304c in different columns in the same row. Increasing the width of backbone 311c may impart additional rigidity to CAF 300c. This, in turn, may allow for the removal of material in another portion of CAF 300c, which may result in a decrease in rigidity of the CAF. Thus, by increasing the width of backbone 311c, and decreasing the width of, for example, body 302c, overall rigidity may be maintained while resulting in a net decrease in size and increase in flexibility of CAF 300c. Eyelets 304c preferably remain large enough to allow a needle carrying a suture to pass through.

Figure 3D:
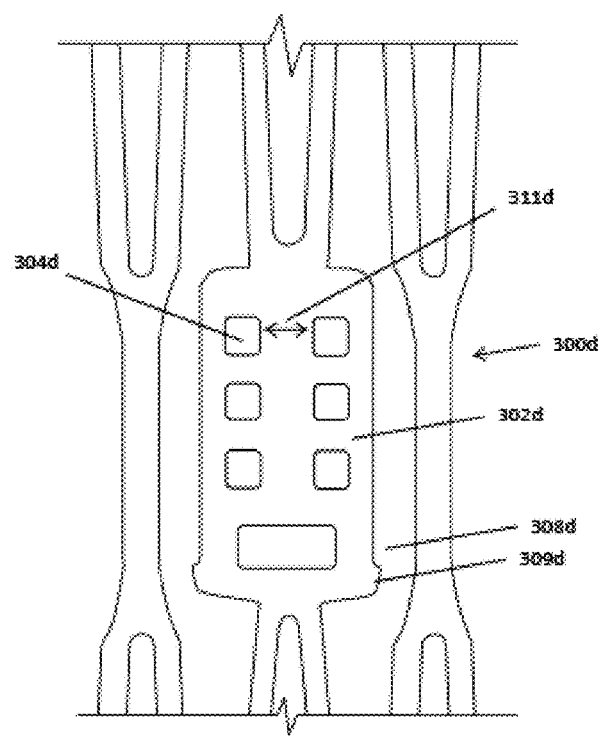

FIG. 3D illustrates a CAF 300d according to an additional embodiment of the disclosure, which is similar to CAF 300c of FIG. 3C with at least one exception. The width of body 302d is decreased in comparison to that of body 302c of CAF 300c, much in the same way body 302b of CAF 300b is narrowed in comparison to body 302a of CAF 300a. This results in a recess 308d extending in the distal direction along the entire length of body 302d or, in other words, a laterally extending protrusion 309d near the proximal end of body 302d. As illustrated, body 302d may include two such protrusions 309d extending laterally in opposite directions from opposing edges of the body. As discussed in relation to CAFs 300b and 300a, the reduced width of body 302d may allow for a smaller crimping profile, while the increased width of backbone 311*d* and the reduced size of eyelets 304*d* provide rigidity body 302*d* having a reduced width.

Figure 3E:
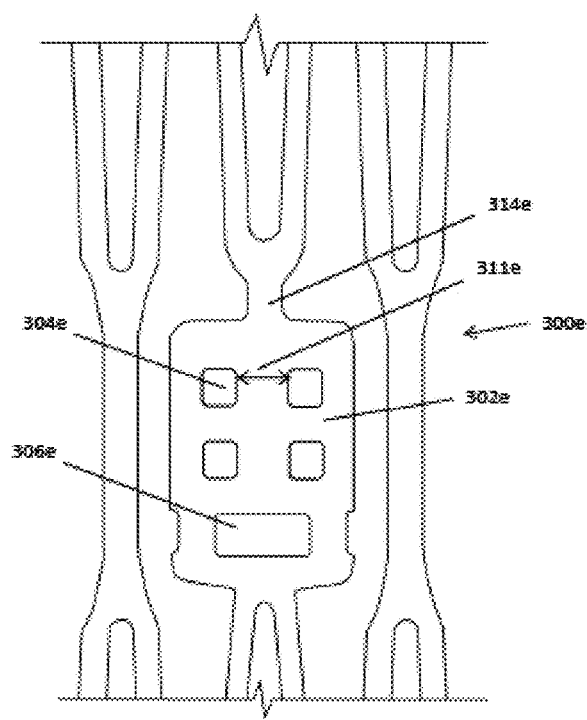

FIG. 3E illustrates a CAF 300*e* according to yet another embodiment of the disclosure. CAF 300*e* is similar to CAF 300*c* of FIG. 3C, with at least one exception. In particular, whereas CAF 300*c* includes three rows and two columns of eyelets 304*c*, CAF 300*e* includes only two rows and two columns of eyelets 304*e* in addition to elongated eyelet 306*e*. Decreasing the height of body 302*e* in comparison to that of body 302*c* of CAF 300*c* may increase the ability of the stent to track in the blood vessels, for example when the stent is delivered across the aortic arch. In addition, two struts 314*e* distal to CAF 300*e* meet and extend proximally as a single strut connecting to the distal end of CAF 300*e*. Although shown with a relatively large backbone 311*e* and relatively small eyelets 304*e*, the eyelets may be larger and the backbone smaller, similar to the configuration illustrated with respect to CAF 300*a* in FIG. 3A.

Figure 3F:
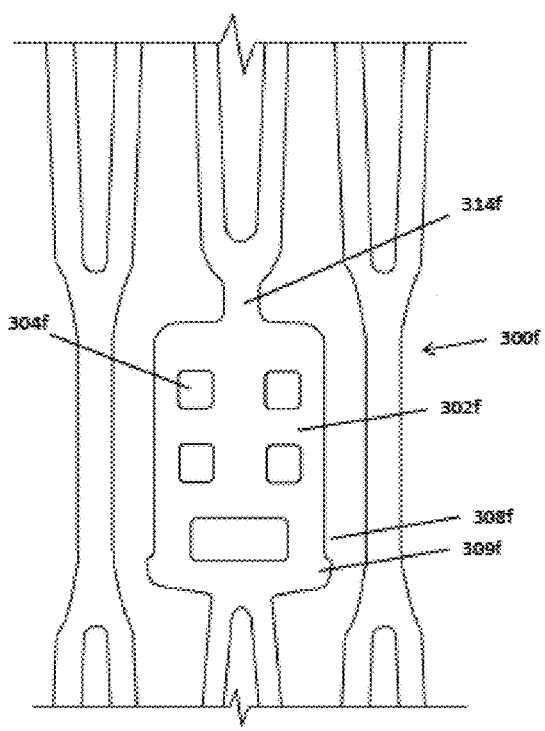

FIG. 3F illustrates a CAF 300*f* according to still another embodiment of the disclosure, which is similar to CAF 300*e* of FIG. 3E with at least one exception. Specifically, CAF 300*f* includes the same configuration of eyelets 304*f* as CAF 300*e*, but has a reduced width body 302*f*, resulting in an extended recess 308*f* or, stated another way, a protrusion 309*f*, similar to some of the embodiments described above. In this embodiment, protrusion 309*f* extends farther laterally from the edge of body 302*f* than any other portion of the edge. The distal end of CAF 300*f* may be attached to a strut 314*f* in a similar configuration to the configuration of CAF 300*e*. This particular embodiment may provide increased tracking ability and reduced crimping profile.

Figure 3G:
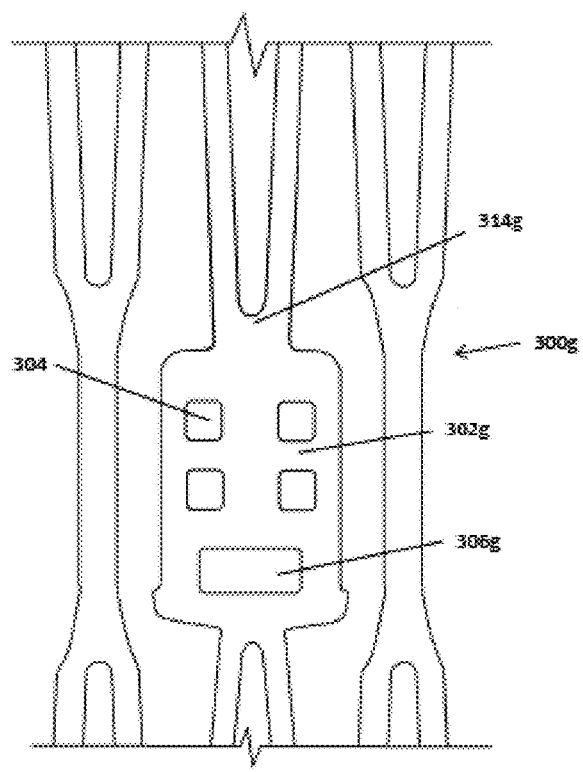

FIG. 3G illustrates a CAF 300*g* according to a further embodiment of the disclosure. CAF 300*g* is similar to CAF 300*f* of FIG. 3F, with at least one exception. The distal end of CAF 300*g* is connected to struts 314*g* that merge with the body 302*g* of CAF 300*g*. This is slightly different than CAF 300*f*, which includes two struts 314*f* that meet distal to body 302*f* and extend to the body as a single strut.

Figure 3H:
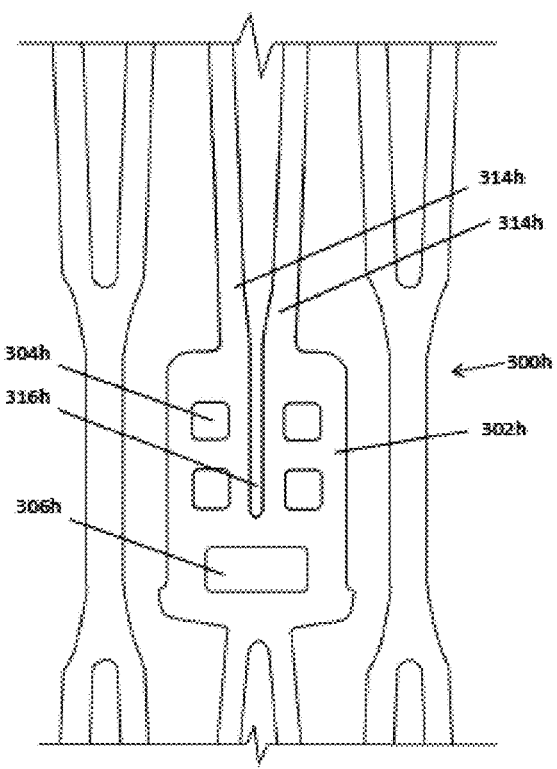

FIG. 3H illustrates a CAF 300*h* according to another embodiment of the disclosure, which is similar to CAF 300*f* of FIG. 3G with at least one exception. In CAF 300*h*, a slot 316*h* extends proximally through body 302*h* from the distal end thereof toward elongated eyelet 306*h*, dividing body 302*h* into two portions. As illustrated, slot 316*h* extends proximally along or nearly along a center longitudinal axis of body 302*h* between the two columns of eyelets 304*h*, stopping short of elongated eyelet 306*h*. Struts 314*h* are connected to the distal end of body 302*h*, one strut 314*h* being connected to one portion of the body and another strut 314*h* being connected to the other portion of the body. Slot 316*h* may provide increased flexibility to CAF 300*h*, allowing, for example, better tracking ability of the stent. In the illustrated embodiment, the increased flexibility and/or tracking ability may result from an increased ability for the stent body to twist as a result of the described features. It should be understood that slot 316*h* may extend more or less proximally than illustrated, for example by only extending to eyelets 304*h* in the most distal row and not extending to eyelets 304*h* in the most proximal row. Alternatively, slot 316*h* may extend more proximally such that the proximal end of the slot is positioned proximally of all eyelets 304*h*. Other aspects of CAF 300*h* may also be varied, including having a non-reduced-width body 302*h*, such as that illustrated in FIG. 3E. Similarly, the number, size, and position of eyelets 304*h* and/or elongated eyelet 306*h* may be varied while retaining the slot 316*h*.

Figure 3I:
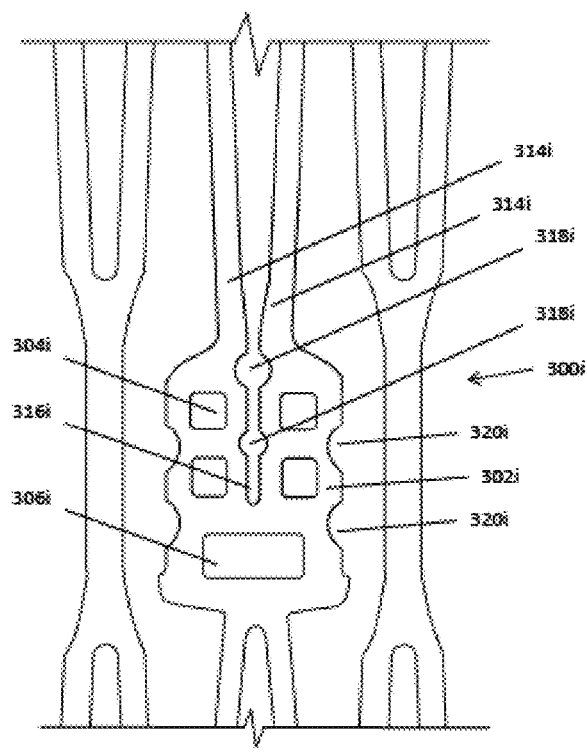

FIG. 3I illustrates a CAF 300*i* according to still a further embodiment of the disclosure. CAF 300*i* is similar to CAF 300*h* of FIG. 3H, with at least one exception. Generally, CAF 300*i* includes a reduced width body 302*i* including two rows and two columns of eyelets 304*i* and an elongated eyelet 306*i*. Similar to CAF 300*h*, CAF 300*i* includes a slot 316*i* extending proximally along body 302*i* between the two columns of eyelets 304*i*, dividing the body into two portions, with a strut 314*i* connected to the distal end of each portion of the body. Unlike other embodiments, however, additional material of body 302*i* may be removed to increase the flexibility of CAF 300*i*. For example, one or more recesses 318*i* may be formed in body 302*i* along the edges of slot 316*i*. As illustrated, two slot recesses 318*i* are formed along slot 316*i*, each slot recess 318*i* being generally circular or semi-circular, although the slot recesses may take other shapes. In other words, each slot recess 318*i* may be thought of as either a semi-circular (or other shaped) recess defined on one side of the slot, or as a circular (or other shaped) recess defined by two opposed slot recesses 318*i*. Also, each slot recess 318*i* is preferably formed so that it does not laterally align, or only partially laterally aligns, with any eyelets 304*i*. That is, in each row of eyelets 304*i*, a proximal and a distal boundary of the eyelets in that particular row define a space between the two boundaries. Because CAF 300*i* includes two rows of eyelets 304*i*, two of these spaces exist, one space corresponding to the eyelets in each row. No slot recess 318*i* is positioned entirely within either of these spaces. By forming slot recesses 318*i* that, at most, only partially align laterally with eyelets 304*i*, the flexibility of CAF 300*i* is increased while still maintaining the structural integrity of body 302*i*, which might be compromised if slot recesses 318*i* fully or mostly aligned laterally with the eyelets.

Body 302*i* may also include body recesses 320*i* along its side edges. As illustrated, body 302*i* includes four body recesses 320*i*, each of which is generally semi-circular shaped, although they may take other shapes. Also as illustrated, body recesses 320*i* are formed on the edges of body 302*i* opposite slot 316*i* such that the body recesses do not laterally align, or only partially laterally align, with any eyelets 304*i* or with elongated eyelet 306*i*. That is, no body recess 320*i* is positioned entirely within any space defined between the proximal and distal boundaries of the eyelets 304*i* in a particular row. Similar to slot recesses 318*i*, by forming body recesses 320*i* that, at most, only partially laterally align with eyelets 304*i* and with elongated eyelet 306*i*, the flexibility of CAF 300*i* is increased while still maintaining the structural integrity of body 302*i*, which might be compromised if body recesses 320*i* fully or mostly aligned laterally with eyelets 304*i* and/or eyelet 306*i*.

Figure 3J:
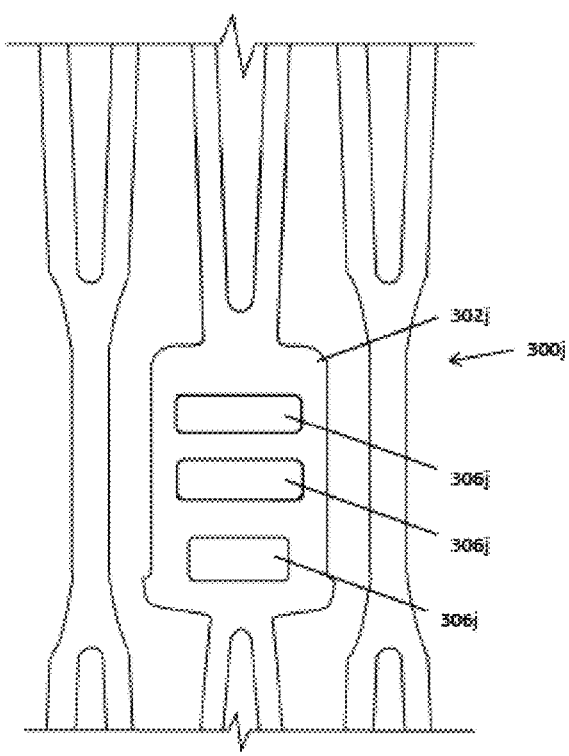

FIG. 3J illustrates a CAF 300*j* according to another embodiment of the disclosure. CAF 300*j* is similar to CAF 300*g* of FIG. 3G, with at least one exception. More particularly, the body 302*j* of CAF 300*j* includes only elongated eyelets 306*j*. In the illustrated embodiment, body 302*j* includes three elongated eyelets 306*j* generally arranged in a single column. The proximalmost elongated eyelet 306*j* may take the general form of a rectangle, while each elongated eyelet 306*j* distal to the proximalmost eyelet may also take the general form of a rectangle, but may be wider than the proximalmost eyelet. Preferably, the two distalmost elongated eyelets 306*j* are substantially identical to one another and all three elongated eyelets 306*j* are centered along a longitudinal axis of body 302*j*. Although the particular number, shape, size, and positioning of elongated eyelets 306*j* may be varied, the illustrated configuration may be desirable for increasing the flexibility of body 302j while maintaining the ability of sutures to be passed through eyelets 306j and secured to the body 302j of CAF 300j.

Figure 4A:
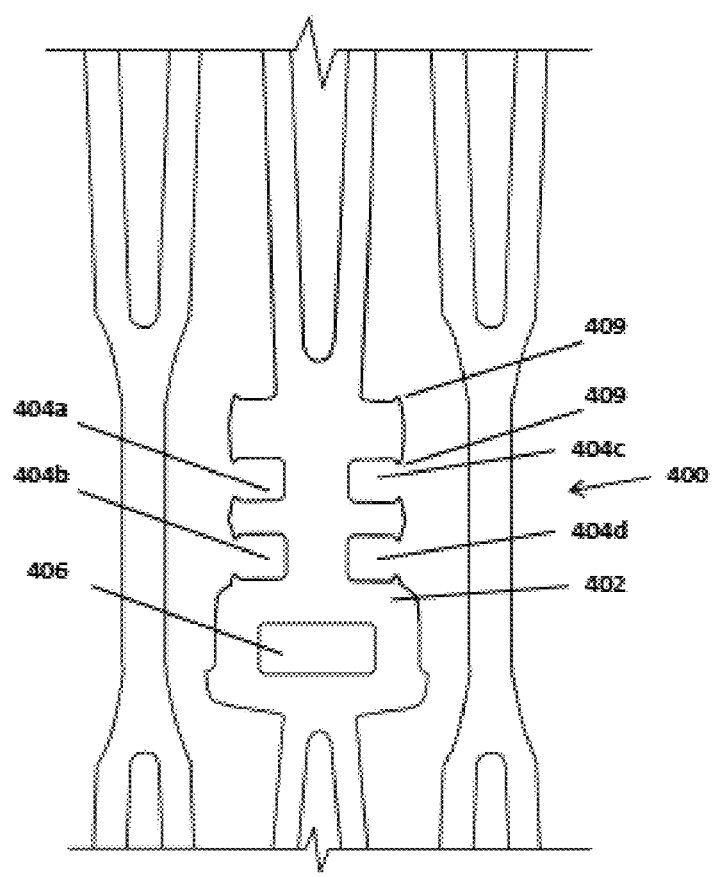
FIG. 4A is a front view of another commissure attachment feature according to an aspect of the disclosure.

FIG. 4A illustrates a CAF 400 according to another embodiment of the disclosure, which is similar to CAF 300g of FIG. 3G with at least one exception. More particularly, portions of body 402 are removed in comparison to body 302g, such that at least some of eyelets 404a-d are enclosed on only three sides. This may be true, for example, if eyelets 404a-d are generally rectangular. In other words, eyelets 404a-d are not fully enclosed by body 402 as they are in the other embodiments described herein. Body 402 may also include a fully enclosed elongated eyelet 406 as in the other embodiments described herein. Body 402 may be formed such that the portions of the body on the proximal and distal sides of each eyelet 404a-d in a column have a protrusion 409 extending generally parallel to the longitudinal axis of the body. Protrusions 409 may help prevent sutures (illustrated in FIG. 4B) attached to body 402 through eyelets 404a-d from slipping off the body. Although not illustrated, CAF 400 may be modified to include a slot, such as that described with respect to CAF 300h or 300i.

FIG. 4B illustrates CAF 400 of FIG. 4A with an exemplary suture pattern from the outer diameter or abluminal side of the stent. FIG. 4C illustrates CAF 400 with the same suture pattern viewed from the inner diameter or lumenal side of the stent. Tabs 451, 461 of two different leaflets 450, 460 are illustrated in FIG. 4C, although they are omitted in FIG. 4B for clarity. Also, in FIG. 4C, much of body 402 of CAF 400 is illustrated in broken lines behind the leaflets 450, 460. The following describes the use of a single suture S to attach leaflets 450, 460 to CAF 400. It will be understood, however, that multiple sutures may be used for this purpose. For example, one suture may attach first leaflet 450 to CAF 400, while a second, separate suture attaches second leaflet 460 to the CAF.

The suture pattern may begin at any point at or near CAF 400 and terminate at any other point. In at least some examples, the suture pattern begins and terminates at the same position. For the sake of illustration, the suture pattern will be described as beginning at point p1, within eyelet 404d. As used herein, with reference to FIG. 4B, the term "out" indicates passing the suture S from the lumenal side of the valve through the tab of the leaflet 450 or 460 and past the stent structure to the abluminal side of the valve. The term "in" indicates passing the suture S from the abluminal side of the valve past the stent structure and through the tab of the leaflet 450 or 460 to the lumenal side of the valve.

The suture pattern may begin by passing a leading end of suture S out through eyelet 404d at point p1. Suture S may then be advanced in through point p2 through leaflet 450 in eyelet 404c, back out through point p3 through the leaflet in eyelet 404d, and finally in through point p4 through the leaflet in eyelet 404c, essentially forming two loops of the suture. Suture S may then be directed up above the top of leaflets 450, 460 and, advanced out from between struts 414 and wrapped around the strut that is nearer eyelets 404c-d. Advancing suture S from point p5 to point p6 in this manner essentially wraps the suture around one of struts 414. Suture S may then be passed behind both struts 414, and wrapped around the other strut by passing the suture out at point p7 and in at point p8, point p8 being positioned between the two struts 414.

From point p8, suture S may be advanced down, passing the leading end of suture S out of eyelet 404a through leaflet 460 at point p9. Then, suture S may be passed in through eyelet 404b through leaflet 460 at point p10, out eyelet 404a through the leaflet at point p11, and back into eyelet 404b and through the leaflet at point p12, forming two loops between eyelets 404a-b. From point p12, the leading end of suture S may be passed out of elongated eyelet 406 through leaflet 460 near point p13 and wrapped around CAF 400 near a protrusion 409 by advancing the suture in through the leaflet near point p14. The leading end of suture S may then be passed out of elongated eyelet 406 through leaflet 460. Then, the trailing end of suture S, which is trailing from the initial point of insertion p1, may be passed out of elongated eyelet 406 through leaflet 450 near point p16. The trailing end of suture S may then be passed into leaflet 450 near another protrusion 409 near point p17. Finally the trailing end of suture S may be passed out of elongated eyelet 406 and leaflet 450. At this point, the leading and trailing ends of suture S may be joined, for example by tying or knotting the ends to secure the suture. The particular suture pattern described above is symmetrical without any cross-over through the leaflets 450, 460, as the cross-over occurs above the free edges 452, 462 of the leaflets around struts 414. This configuration may result in less or no interference with movement of the free edges of the leaflets with reduced abrasion while maintaining a secure connection between the leaflets 450, 460 and CAF body 400. Also, this configuration allows for maintaining a secure connection without the need for a third proximal row of eyelets.

For CAF 400, since the suture S runs generally vertically up the body 402 of the CAF, eyelets 404a-d may be open on one side without significantly affecting the stability of the sutures. As described above in relation to FIG. 4A, protrusions 409 may help suture S resist slipping laterally out from eyelets 404a-d. Other suture patterns are described in greater detail in U.S. patent application Ser. No. 13/781,201, the entire contents of which are hereby incorporated by reference herein.

Figure 4D:
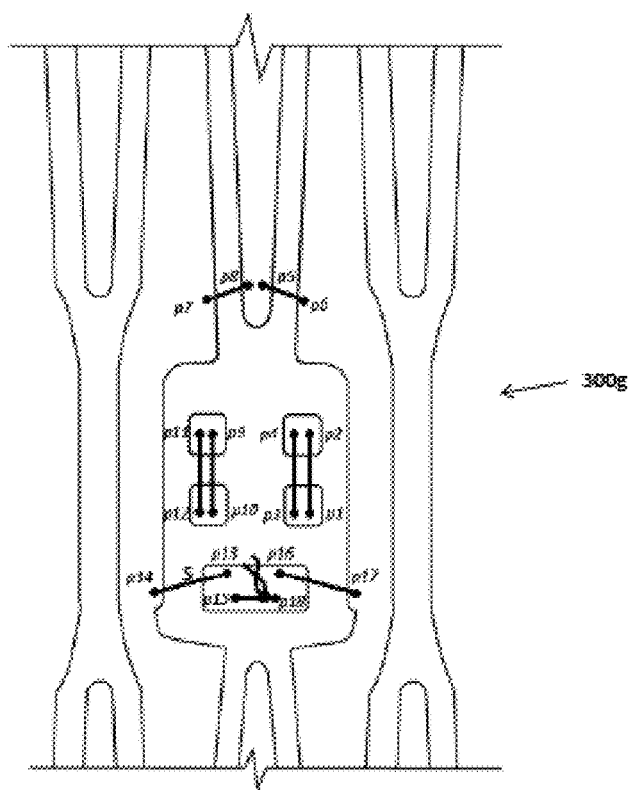
FIG. 4D is a front view of suture attachments on the commissure attachment feature of FIG. 3G.
Figure 4E:
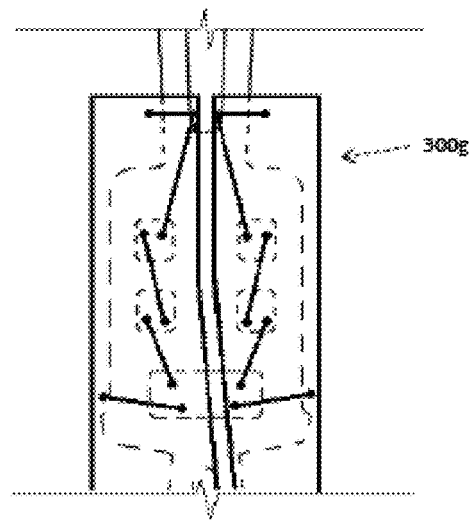
FIG. 4E is a rear view of the suture attachments in FIG. 4D.

It should also be noted that, although other suture patterns may be used for CAF 400 or any other CAF described herein, the same suture pattern described with respect to CAF 400 may be used for other CAFs described herein. For example, CAF 300g is illustrated in FIGS. 4D-E with the identical suture pattern as described in relation to CAF 400.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. It will be appreciated that the various dependent claims and the features set forth therein can be combined in different ways than presented in the initial claims. It will also be appreciated that the features described in connection with individual embodiments may be shared with others of the described embodiments.

The following Paragraphs summarize certain aspects of the disclosure.

Paragraph A: A prosthetic heart valve, comprising: a collapsible and expandable stent having a proximal end and a distal end, the stent including a plurality of struts defining a plurality of open cells; a plurality of commissure attachment features disposed on the stent, each commissure attachment feature including a body and a plurality of eyelets arranged in at least two rows and at least two columns, the body including a slot extending from a distal end of the body between two of the columns of eyelets toward a proximal end of the body, the slot dividing the body into a first portion and a second portion; and a collapsible and expandable valve assembly including a plurality of leaflets connected to the plurality of commissure attachment features, wherein at least one of the struts is connected to a distal end of the first portion of the body, and at least another of the struts is connected to a distal end of the second portion of the body.

Paragraph B: The prosthetic heart valve of Paragraph A, wherein the slot extends along a longitudinal axis of the body.

Paragraph C: The prosthetic heart valve of Paragraph A, wherein the body includes an elongated eyelet positioned proximally of the plurality of eyelets.

Paragraph D: The prosthetic heart valve of Paragraph C, wherein a proximal end of the slot is positioned distal to the elongated eyelet.

Paragraph E: The prosthetic heart valve of Paragraph D, wherein the proximal end of the slot is positioned proximally of the plurality of eyelets.

Paragraph F: The prosthetic heart valve of Paragraph C, wherein a proximal end of the slot is positioned distal to the eyelets in at least one row.

Paragraph G: The prosthetic heart valve of Paragraph A, further comprising a first slot recess positioned in the slot.

Paragraph H: The prosthetic heart valve of Paragraph G, wherein the first slot recess is generally semi-circular and formed in the first portion of the body.

Paragraph I: The prosthetic heart valve of Paragraph G, wherein the first slot recess includes a first generally semi-circular recess portion formed in the first portion of the body and a second generally semi-circular recess portion formed in the second portion of the body.

Paragraph J: The prosthetic heart valve of Paragraph I, wherein, for each row of eyelets, a space is defined between a proximal boundary of each eyelet in the row and a distal boundary of each eyelet in the row, and the first slot recess is not positioned entirely within any of the spaces.

Paragraph K: The prosthetic heart valve of Paragraph I, further comprising a second slot recess positioned in the slot, the second slot recess including a third generally semi-circular recess portion formed in the first portion of the body and a fourth generally semi-circular recess portion formed in the second portion of the body.

Paragraph L: The prosthetic heart valve of Paragraph K, wherein, for each row of eyelets, a space is defined between a proximal boundary of each eyelet in the row and a distal boundary of each eyelet in the row, and neither the first slot recess nor the second slot recess is positioned entirely within any of the spaces.

Paragraph M: The prosthetic heart valve of Paragraph A, further comprising a first body recess formed in a first edge of the body opposite the slot, the first body recess being generally semi-circular.

Paragraph N: The prosthetic heart valve of Paragraph M, wherein, for each row of eyelets, a space is defined between a proximal boundary of each eyelet in the row and a distal boundary of each eyelet in the row, and the first body recess is not positioned entirely within any of the spaces.

Paragraph O: The prosthetic heart valve of Paragraph M, further comprising a second body recess formed in a second edge of the body opposite the slot, the second body recess being generally semi-circular.

Paragraph P: The prosthetic heart valve of Paragraph O, wherein, for each row of eyelets, a space is defined between a proximal boundary of each eyelet in the row and a distal boundary of each eyelet in the row, and neither the first body recess nor the second body recess is positioned entirely within any of the spaces.

Paragraph Q: The prosthetic heart valve of Paragraph A, wherein the plurality of eyelets comprises four eyelets arranged in two rows and two columns and a fifth elongated eyelet positioned proximally of the four eyelets.

Paragraph R: The prosthetic heart valve of Paragraph A, further comprising: a first protrusion near a proximal end of the body, the first protrusion extending laterally from a first edge of the body in a first direction; and a second protrusion near the proximal end of the body, the second protrusion extending laterally from a second edge of the body in a second direction opposite the first direction.

Paragraph S: The prosthetic heart valve of Paragraph R, wherein the first protrusion extends farther laterally from the first edge of the body than any other portion of the first edge of the body and the second protrusion extends farther laterally from the second edge of the body than any other portion of the second edge of the body.

Paragraph T: The prosthetic heart valve of Paragraph A, wherein the proximal end of body includes at least one projection extending circumferentially away from a longitudinal axis of the body farther than any other portion of the body.

Paragraph U: A prosthetic heart valve, comprising: a collapsible and expandable stent having a proximal end and a distal end, the stent including a plurality of struts defining a plurality of open cells; a plurality of commissure attachment features disposed on the stent, each commissure attachment feature including a body having a longitudinal axis and a plurality of eyelets arranged in one column, the plurality of eyelets including a generally rectangular proximalmost eyelet and at least two generally rectangular eyelets positioned distal to the proximalmost eyelet, the at least two distal eyelets each being wider than the proximalmost eyelet; and a collapsible and expandable valve assembly including a plurality of leaflets connected to the plurality of commissure attachment features.

Paragraph V: The prosthetic heart valve of Paragraph U, wherein the proximalmost eyelet and the at least two distal eyelets are each centered along the longitudinal axis of the body.

Paragraph W: The prosthetic heart valve of Paragraph U, wherein the at least two distal eyelets are substantially identical to one another.

Paragraph X: The prosthetic heart valve of Paragraph U, wherein a proximal end of the body includes at least one projection extending circumferentially away from the longitudinal axis of the body farther than any other portion of the body.

Paragraph Y: A prosthetic heart valve, comprising: a collapsible and expandable stent having a proximal end and a distal end, the stent including a plurality of struts defining a plurality of open cells; a plurality of commissure attachment features disposed on the stent, each commissure attachment feature including a body having a longitudinal axis and a plurality of eyelets arranged in at least two rows and at least two columns, at least one of the eyelets having an open side; and a collapsible and expandable valve assembly including a plurality of leaflets connected to the plurality of commissure attachment features.

Paragraph Z: The prosthetic heart valve of Paragraph Y, wherein at least four of the plurality of eyelets are generally rectangular, each of the at least four eyelets having an open side.

Paragraph AA: The prosthetic heart valve of Paragraph Z, further comprising protrusions on portions of the body on proximal and distal sides of each of the at least four eyelets, the protrusions extending generally parallel to the longitudinal axis of the body adjacent the open sides of the eyelets.

Paragraph BB: The prosthetic heart valve of Paragraph Y, wherein a proximal end of the body includes at least one projection extending circumferentially away from the longitudinal axis of the body farther than any other portion of the body.

The invention claimed is:

1. A prosthetic heart valve, comprising:
a collapsible and expandable stent having proximal end and a distal end, the stent including a plurality of struts defining a plurality of open cells, and a plurality of commis sure attachment features; and
a collapsible and expandable valve assembly including a plurality of leaflets connected to the plurality of commissure attachment features, the valve assembly adapted to allow blood to flow from the proximal end to the distal end, and to substantially block blood from flowing from the distal end to the proximal end,
wherein each commissure attachment feature includes a body having first and second side edges extending in a longitudinal direction from the proximal end of the stent to the distal end of the stent and a longitudinal axis positioned between the two side edges and extending in the longitudinal direction of the stent, a first eyelet formed as a first recess in the first side edge extending toward the longitudinal axis, a second eyelet formed as a second recess in the second side edge extending toward the longitudinal axis, a third eyelet formed as a third recess in the first side edge extending toward the longitudinal axis, and a fourth eyelet formed as a fourth recess in the second side edge extending toward the longitudinal axis, such that the first, second, third, and fourth eyelets are not fully enclosed by the body, the first and third eyelets being directly adjacent each other in the longitudinal direction and separated by a first portion of the body, the second and fourth eyelets being directly adjacent each other in the longitudinal direction and separated by a second portion of the body;
wherein a first portion of a suture member passes through a first one of the plurality of leaflets and through the first eyelet, wraps around the first portion of the body, and passes through the third eyelet, and a second portion of the suture member passes through a second one of the plurality of leaflets and through the second eyelet, wraps around the second portion of the body, and passes through the fourth eyelet.

2. The prosthetic heart valve of claim 1, wherein the first and second eyelets are each formed by first and second interior edges of the body extending in a direction substantially perpendicular to the longitudinal direction of the stent, and a third interior edge extending in a direction substantially parallel to the longitudinal direction of the stent.

3. The prosthetic heart valve of claim 2, wherein the first interior edges of the body include protrusions adjacent the side edges of the body extending in a direction toward the second interior edges.

4. The prosthetic heart valve of claim 2, wherein the second interior edges of the body include protrusions adjacent the side edges of the body extending in a direction toward the first interior edges.

5. The prosthetic heart valve of claim 2, wherein the first interior edges of the body include first protrusions adjacent the side edges of the body extending in a direction toward the second interior edges of the body, and the second interior edges of the body include second protrusions adjacent the side edges of the body extending in a direction toward the first interior edges of the body.

6. The prosthetic heart valve of claim 1, wherein the body includes a rectangular eyelet formed by four interior edges of the body.

7. The prosthetic heart valve of claim 6, wherein the rectangular eyelet is positioned proximal to the first and second eyelets.

8. The prosthetic heart valve of claim 1, wherein a proximal end of the body includes a first projection extending circumferentially away from the longitudinal axis of the body.

9. The prosthetic heart valve of claim 8, wherein the proximal end of the body includes a second projection extending circumferentially away from the longitudinal axis of the body, the first and second projections being positioned on opposite sides of the longitudinal axis of the body.

10. The prosthetic heart valve of claim 8, wherein the first projection extends circumferentially farther away from the longitudinal axis of the body than any other portion of the body.

11. The prosthetic heart valve of claim 1, wherein the body includes a distal end having a first projection adjacent the first side edge extending toward the distal end of the stent.

12. The prosthetic heart valve of claim 11, wherein the distal end of the body has a second projection adjacent the second side edge extending toward the distal end of the stent.

* * * * *